(12) United States Patent
Bailey et al.

(10) Patent No.: US 12,364,497 B2
(45) Date of Patent: Jul. 22, 2025

(54) METHOD FOR TUNING LITHOTRIPSY FREQUENCY TO TARGET SIZE

(71) Applicant: University of Washington, Seattle, WA (US)

(72) Inventors: Michael R. Bailey, Seattle, WA (US); Adam D. Maxwell, Seattle, WA (US); Oleg A. Sapozhnikov, Seattle, WA (US)

(73) Assignee: University of Washington, Seattle, WA (US)

( * ) Notice: Subject to any disclaimer, the term of this patent is extended or adjusted under 35 U.S.C. 154(b) by 481 days.

(21) Appl. No.: 17/937,294

(22) Filed: Sep. 30, 2022

(65) Prior Publication Data

US 2023/0104557 A1 Apr. 6, 2023

Related U.S. Application Data

(60) Provisional application No. 63/251,146, filed on Oct. 1, 2021.

(51) Int. Cl.
*A61B 17/22* (2006.01)
*A61B 17/225* (2006.01)
*A61B 17/00* (2006.01)

(52) U.S. Cl.
CPC .............. *A61B 17/2256* (2013.01); *A61B 2017/00141* (2013.01); *A61B 2017/00146* (2013.01); *A61B 2017/00402* (2013.01)

(58) Field of Classification Search
CPC ... A61B 17/2256; A61B 17/22; A61B 17/225; A61B 2017/00141; A61B 2017/00146;
(Continued)

(56) References Cited

U.S. PATENT DOCUMENTS

| 5,158,070 A | 10/1992 | Dory |
| 9,901,753 B2 | 2/2018 | Cain |

(Continued)

FOREIGN PATENT DOCUMENTS

| CN | 102144936 | 8/2011 |
| JP | 794982 | 4/1995 |
| JP | 200370798 | 3/2003 |

OTHER PUBLICATIONS

Maxwell, A.D., et al., "Fragmentation of Urinary Calculi in Vitro by Burst Wave Lithotripsy," The Journal of Urology 193(1):338-344, Jan. 2015.

(Continued)

*Primary Examiner* — Anh T Dang
(74) *Attorney, Agent, or Firm* — Christensen O'Connor Johnson Kindness PLLC

(57) ABSTRACT

Methods and systems for tuning lithotripsy frequency to target size are disclosed. In one embodiment, a lithotripsy system for comminuting a stone in a body includes: a burst wave lithotripsy (BWL) therapy transducer configured to transmit smooth ultrasound waves within a burst of ultrasound waves toward the stone; and a controller configured to determine operating frequency of the ultrasound waves of the therapy transducer. The operating frequency of the ultrasound waves is determined as:

$$f = Const. \frac{c}{d}$$

where:
d is a diameter of the stone,
f is the frequency of the ultrasound waves, (Continued)

c is a wave speed in the stone, and
Const. is a predetermined constant.

21 Claims, 10 Drawing Sheets

(58) Field of Classification Search
CPC .......... A61B 2017/00402; A61B 2017/00172; A61B 2017/22009; A61N 2007/0056; A61N 2007/006
See application file for complete search history.

(56) References Cited

U.S. PATENT DOCUMENTS 10,251,657 B1 4/2019 Maxwell
2021/0322040 A1 10/2021 Gavala

OTHER PUBLICATIONS

Harper, J.D., et al., "First In-Human Burst Wave Lithotripsy for Kidney Stone Comminution: Initial Two Case Studies," Journal of Endourology 35(4):506-511, 2021.
Cleveland, R.O., et al., "Modeling elastic wave propagation in kidney stones with application to shock wave lithotripsy," The Journal of the Acoustical Society of America 118(4):2667-2676, 2005.
Ramesh, S. et al., "In Vitro Evaluation of Urinary Stone Comminution with a Clinical Burst Wave Lithotripsy System," Journal of Endourology 34(11):1167-1173, 2020.
Eisenmenger, W., "The mechanisms of stone fragmentation in ESWL," Ultrasound in Medicine and Biology 27(5):683-693, 2001.
Zhang, Y., et al., "Effects of Stone Size on the Comminution Process and Efficiency in Shock Wave Lithotripsy," Ultrasound in Medicine & Biology 42(11):2662-2675, 2016.
Maxwell, A.D., et al., "An investigation of elastic waves producing stone fracture in burst wave lithotripsy," The Journal of the Acoustical Society of America 147(3):1607-1622, Mar. 2020.
Williams Jr., J.C., et al., "Micro-computed tomography for analysis of urinary calculi," Urological Research 38(6):477-487, 2010.
Sapozhnikov, O.A., et al., "Modeling of photoelastic imaging of mechanical stresses in transparent solids mimicking kidney stones," The Journal of the Acoustical Society of America 147(6):3819-3829, 2020.
Cao, S. et al., "Shock-Induced Damage and Dynamic Fracture in Cylindrical Bodies Submerged in Liquid," International Journal of Solids and Structures 169:55-71, 2019.
Zhong, P., et al., "Propagation of shock waves in elastic solids caused by cavitation microjet impact. II: Application in extracorporeal shock wave lithotripsy," The Journal of the Acoustical Society of America 94(1):29-36, 1993.
Cohen, N.P., and H.N. Whitfield, "Mechanical testing of urinary calculi," World Journal of Urology 11:13-18, 1993.
Zarse, C.A., et al., "CT visible internal stone structure-but not Hounsfield unit value-of calcium oxalate monohydrate (COM) calculi predicts lithotripsy fragility in vitro," Urological research 35(4):201-206, 2007.

Randad, A., et al., "Design, fabrication, and characterization of broad beam transducers for fragmenting large renal calculi with burst wave lithotripsy," The Journal of the Acoustical Society of America 148(1), 2020.
Harper, J.D., et al., "First in human clinical trial of ultrasonic propulsion of kidney stones," Journal of Urology 195(4):956-964, 2016.
Sapozhnikov, O.A., et al., "Maximizing mechanical stress in small urinary stones during burst wave lithotripsy," The Journal of the Acoustical Society of America 150(6):4203-4212, 2021.
Moghimnezhad, M., et al., "Numerical Investigation of Burst Wave Lithotripsy and Synthesis of Shock and Burst Waves," AUT Journal of Modeling and Simulation 52(2): 145-156, 2020.
Bailey, M. R., et al., "Improving Burst Wave Lithotripsy Effectiveness for Small Stones and Fragments by Increasing Frequency: Theoretical Modeling and Ex Vivo Study," Journal of Endourology 36(7), 2022, 22 pages.
Hunter, C., et al., "Impact of stone type on cavitation in burst wave lithotripsy," Proceedings of the 176th Meeting of Acoustical Society of America, Nov. 5-9, 2018, Victoria, Canada, POMA vol. 35, 8 pages.
Maeda, K., "Simulation, experiments, and modeling of cloud cavitation with application to burst wave lithotripsy," Doctoral Thesis, California Institute of Technology, May 3, 2018, 150 pages.
Mihradi, S., et al., "Numerical Analysis of Kidney Stone Fragmentation by Short Pulse Impingement," JSME International Journal, Series A 47(4):581-590, 2004.
Anderson, B.E., et al., "Comparison and visualization of focusing wave fields from various time reversal techniques in elastic media," The Journal of the Acoustical Society of America Express Letters 134(6):EL527-EL533, 2013.
Ikeda, T., et al., "Focused Ultrasound and Lithotripsy," Therapeutic Ultrasound, Advances in Experimental Medicine and Biology vol. 880, Chapter 7, pp. 113-129, 2016.
Randad, A.P., "Design, Fabrication and Characterization of Ultrasound Transducers for Fragmenting Large Renal Calculi," Master's Thesis, University of Washington, 2018, 104 pages.
Xiang, G., et al., "Variations of stress field and stone fracture produced at different lateral locations in a shockwave ithotripter field," The Journal of the Acoustical Society of America 150(2):1013-1029, 2021.
Sapozhnikov, O.A., et al., "A mechanistic analysis of stone fracture in lithotripsy," The Journal of the Acoustical Society of America 121(2):1190-1202, 2007.
Maxwell, A.D., et al., "Generation of guided waves during burst wave lithotripsy as a mechanism of stone fracture," The Journal of the Acoustical Society of America, vol. 144(3_Supplement) 2018, Abstract.
Maxwell, A. et al., "Design and adaptation of burst wave lithotripsy to treat small ureteroliths in pet cats," Meeting of the Research on Calculus Kinetics Society, University of Washington, 16 pages.
Chen, T.T., et al., "Burst Wave Lithotripsy and Acoustic Manipulation of Stones," Current Opinions in Urology 30(2):149-156, 2020.
Church, C., et al., American Institute of Ultrasound in Medicine Bio-effects Literature Review of "Prenatal Exposure to Ultrasound Waves Impacts Neuronal Migration in Mice" (E. S. B. Ang, Jr., et al., PNAS 103:12903-12910, 2006.) Journal of Ultrasound in Medicine 28(4):558-561, 2009.

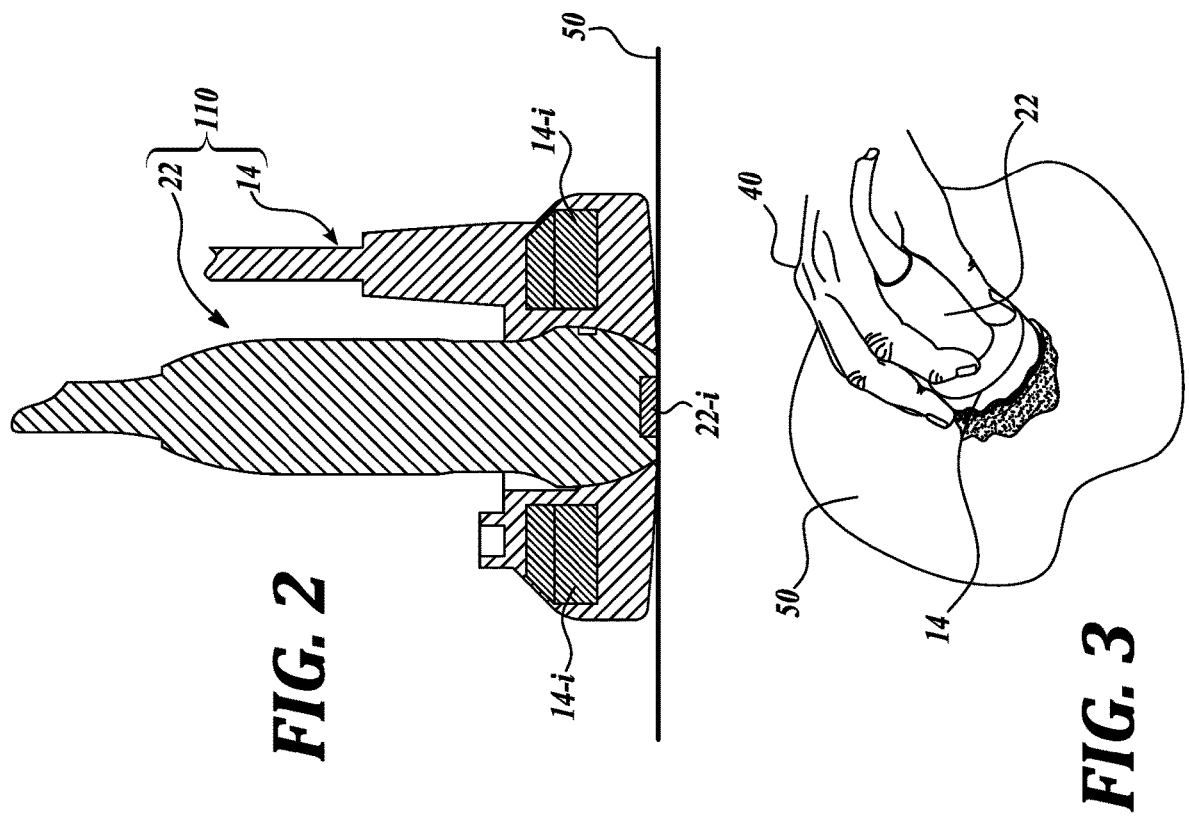
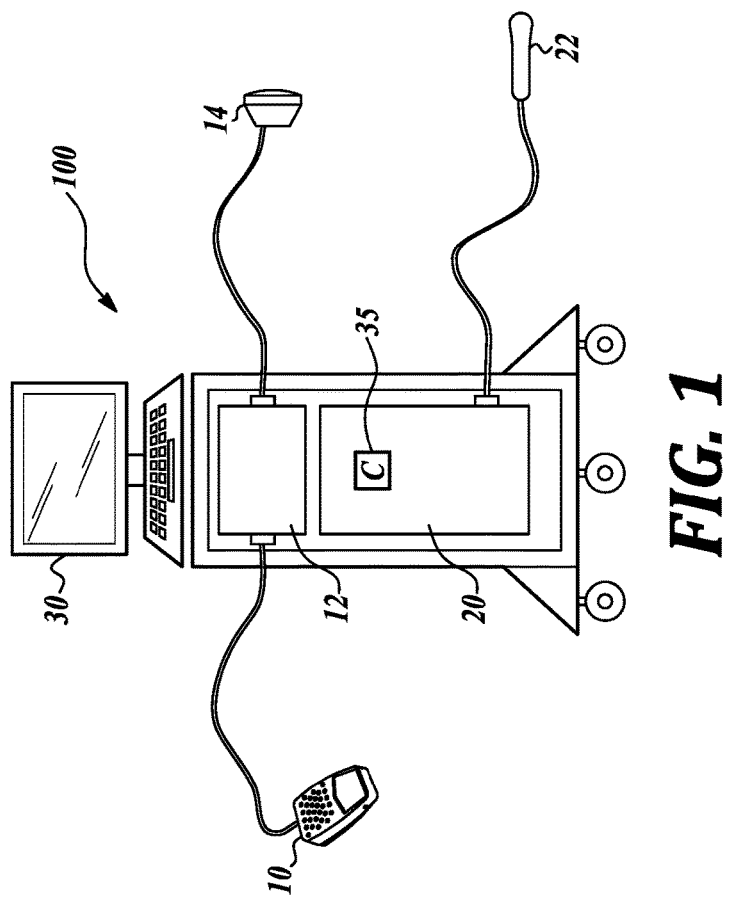

AXIAL PRINCIPAL STRESS
$$T_{zz} = T_I$$
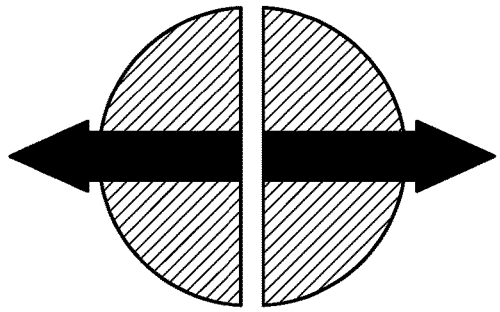
LATERAL PRINCIPAL STRESS
$$T_{rr} = T_{II} = T_{III}$$
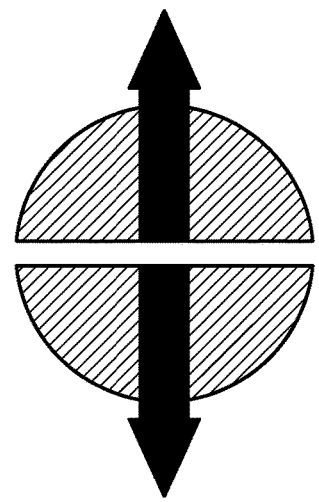
FIG. 5A
FIG. 5B
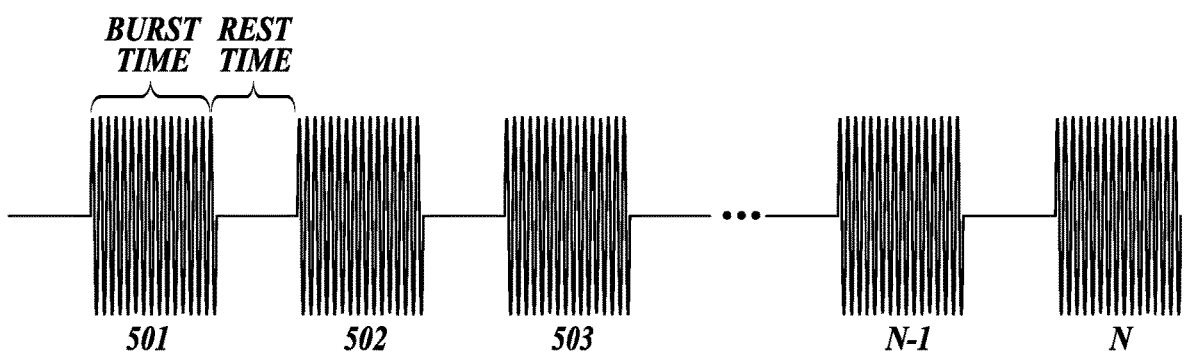
FIG. 6A

US 12,364,497 B2

METHOD FOR TUNING LITHOTRIPSY FREQUENCY TO TARGET SIZE

CROSS-REFERENCE TO RELATED APPLICATION

This application claims the benefit of U.S. Provisional Application No. 63/251,146, filed Oct. 1, 2021, the disclosure of which is expressly incorporated herein by reference in its entirety.

STATEMENT OF GOVERNMENT LICENSE RIGHTS

This invention was made with government support under Grant No. P01 DK043881, awarded by the National Institutes of Health (NIH). The government has certain rights in the invention.

BACKGROUND

Acoustic waves can transfer energy to cause heating of targets placed in an acoustic field, impart radiation forces on object placed in the field, and induce mechanical effects that can damage or break solids including soft tissue or even solids such as kidney stones. Therefore, ultrasound has therapeutic applications such as removal of tumors, drug delivery, tissue heating, and manipulation of urinary stones or foreign objects toward their removal. These applications are achieved by developing ultrasound beam or acoustic beam of desired intensity and shape. For instance, shaping of the ultrasound beam allows focusing of acoustic energy to a confined region of interest where the tumor tissue is targeted for treatment, the accelerated exchange of ultrasound energy for tissue heating, the enhancement of drug delivery to a specific region, and creation of pressure cages that can surround and manipulate objects in the body. Furthermore, a choice of ultrasound frequency, amplitude, duty factor, phase, duration of treatment, etc., determines the resulting effects of the ultrasound on the target object.

In some ultrasound technologies, an ultrasound-based burst wave lithotripsy (BWL) system can be used for fragmenting stones in awake subjects. Unlike shock wave lithotripsy (SWL), which uses a single broadband pulse of ultrasound to fragment stones, the BWL employs narrowband pulses consisting of multiple cycles of ultrasound. As a result, the amplitude of BWL pulse is lower than with SWL, which may enable an office-based BWL procedure. However, methods and systems are still needed for applying the therapeutic ultrasound that imparts desired effects on the target tissue (e.g., breaking a body stone) without unwanted side-effects (e.g., excessive heating of the surrounding tissue, too slow fracturing of the target, etc.).

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a partially schematic view of an ultrasound system in accordance with embodiments of the present technology;

FIG. 2 is a cross-sectional view of an ultrasound probe in accordance with embodiments of the present technology;

FIG. 3 is an isometric view of an ultrasound probe in operation in accordance with embodiments of the present technology;

FIGS. 5A and 5B illustrate principal stresses in an object in accordance with embodiments of the present technology;

FIG. 6A is a graph of BWL bursts in accordance with embodiments of the present technology;

DETAILED DESCRIPTION

Figure 4A:
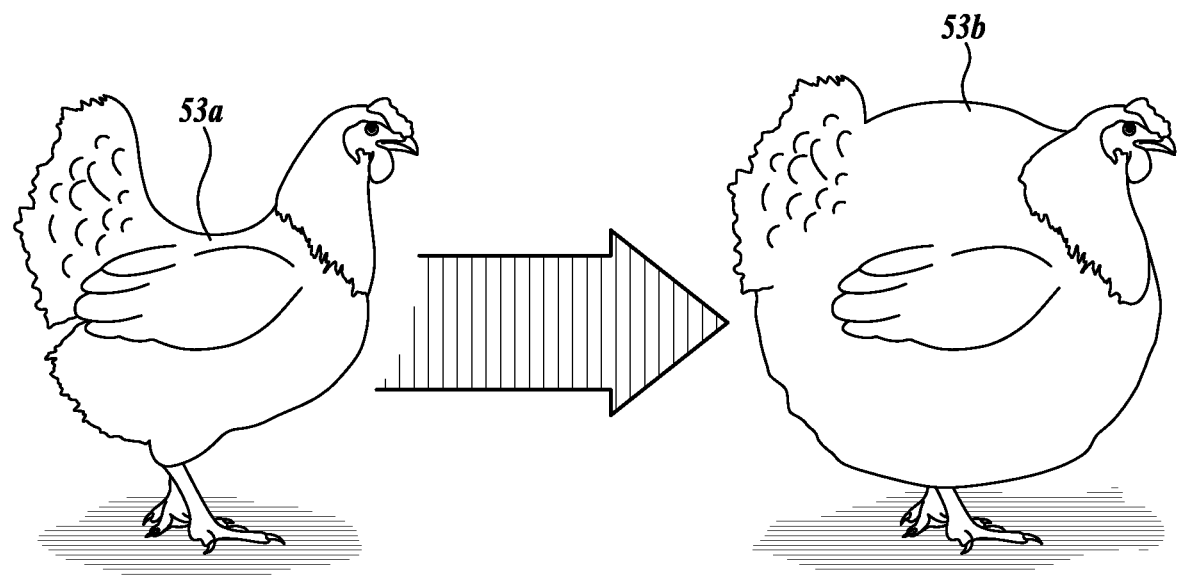
FIGS. 4A and 4B illustrate mathematical mappings of objects to more spherical objects in accordance with embodiments of the present technology.

While illustrative embodiments have been illustrated and described, it will be appreciated that various changes can be made therein without departing from the spirit and scope of the invention.

Unlike shock wave lithotripsy, burst wave lithotripsy (BWL) uses tone bursts, consisting of multiple periods of a sinusoidal wave. In this inventive technology, inventors have established an analytical theoretical approach to modeling mechanical stresses in a spherical stone to assess the dependence of frequency and stone size on stress generated in the stone. The inventors have found that at low frequencies, when the wavelength is greater than the diameter of the stone, the maximum principal stress is approximately equal to the pressure amplitude of the incident wave. With increasing frequency, when the diameter of the stone begins to exceed about half the wavelength in the surrounding liquid (the exact condition depends on the material of the stone), the maximum stress increases and can become more than 6 times greater than the incident pressure. These results suggest that the BWL frequency can be increased for small stones in order to improve the likelihood and rate of fragmentation.

The inventive technology is generally directed to using variable ultrasound frequencies in relation to stone size. Using a linear elastic numerical model, a relationship is defined between a characteristic size of the target object and burst wave lithotripsy (BWL) frequency which may amplify the applied pressure several times in the stone. Aside from this optimal frequency, a frequency too high or too low results in significantly less amplification, if any. The relationship discovered by the inventor can be described as:

(diameter of the target object)*(frequency of the BWL wave)/the shear wave speed=approximately ¾ (or another constant, depending on what wave speed is used).

Furthermore, the inventors have found that the above threshold frequency works well on the larger target objects too (i.e., stones that are larger than the threshold diameter). Stated differently, higher frequencies continue to break larger stones and create the stress amplification within the stone, just not at the center of the stone, whereas lower frequencies do not result in the same amplification.

Additionally, in some embodiments of the inventive technology, an application of at least three cycles in the BWL works well, and more cycles may further amplify the stresses. In some embodiments, a large stone is treated first at one frequency and when as the stone breaks, a higher frequency is used to further fracture the stone fragments.

Some embodiments of the present technology use probes of different frequencies to this end.

FIG. 1 is a partially schematic view of an ultrasound system 100 in accordance with embodiments of the present technology. The ultrasound system 100 includes a therapy probe 14 and an imaging probe 22. The therapy probe 14 can incorporate one or more piezoelectric transducer elements 14i that expand and contract with the changing polarity of electrical voltage applied to the transducer. Such a change in polarity can be generated at a target ultrasound frequency by an alternating current (AC) generator 12. In operation, the therapy transducer 14i vibrates at a prescribed frequency of the therapy ultrasound (corresponding to the AC frequency) when activated by a therapy trigger module 10. These vibrations generate ultrasound waves that propagate through the body and toward a target object (e.g., a kidney stone). The ultrasound may be focused onto the target object by a lens attached to the therapy transducer 14i or by the shaped surface of the therapy transducer itself.

The illustrated ultrasound system 100 includes an imaging probe 22 incorporating one or more piezoelectric transducer elements 22i. In the illustrated embodiment, the operation of the imaging probe 22 is analogous to that of the therapy probe 14. Namely, the imaging transducer elements 22i also transmit ultrasound waves toward the object of interest, but typically at a frequency that is different from that of the therapy transducer. When the imaging ultrasound waves impinge on the object of interest (e.g., a kidney stone) and reflect back toward the piezoelectric elements 22i of the imaging probe 22, the reflected ultrasound waves generate AC signals in the imaging transducer elements 22i. These AC signals are processed by an imaging system 20, and are displayed on a display 30 of the system to provide an indication of, for example, shape, location, or motion of the object of interest or the surrounding tissue. However, in other embodiments the ultrasound system may not include the imaging probe and/or may rely on non-ultrasound imaging techniques. Operation of the system (e.g., choice of frequency, amplitude, duty factor, etc., of the ultrasound) may be controlled by a controller 35.

In some systems, the therapy probe and imaging probe are coupled to form a combined probe. An example of such combined probe is illustrated in FIG. 2 where an ultrasound probe 110 includes the therapy probe 14 and the imaging probe 22. The therapy probe 14 and the imaging probe 22 may take turns when operating to reduce interference between the therapy and imaging ultrasound.

FIG. 3 is an isometric view of a combined ultrasound probe in operation in accordance with conventional technology. In use, an operator 40 holds a handle 16 to aim the combined ultrasound probe 110 toward the target object in a patient 50. This targeting may be based on the information obtained by the imaging probe 22. The operator 40 typically adjusts the aim by adjusting position and/or angle to the ultrasound transducer 110 from time to time.

Figure 4B:
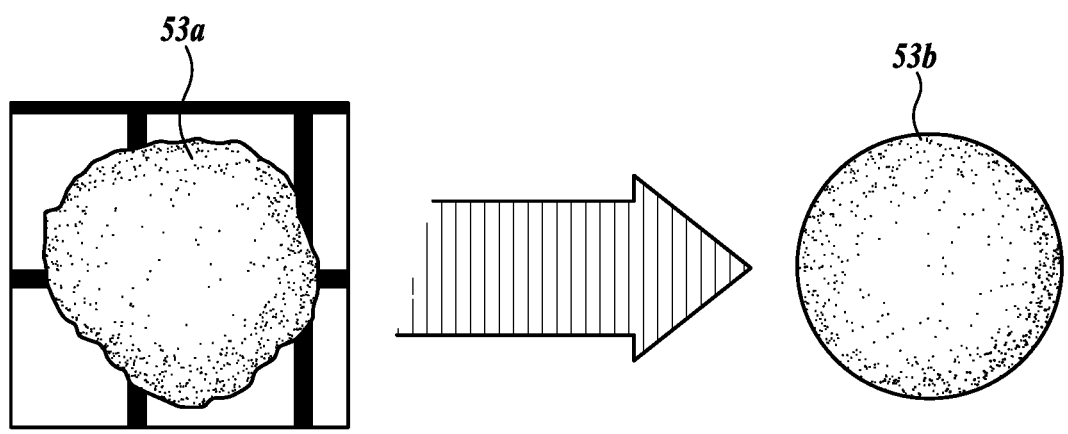

FIGS. 4A and 4B illustrate mathematical mappings of objects to more spherical objects in accordance with embodiments of the present technology. In some embodiments, a nonspherical object 53a can be mathematically mapped into a spherical (or close to spherical) object 53b. This enables a mathematical modeling of the real object as a spherical object, followed by, if needed, a re-mapping the spherical object back to the original shape of the object. Both spherical and nonspherical geometries are representative of actual kidney stones, although in clinical practice, the shape of a patient's stone can only be estimated from, for example, computed tomography with a resolution on the order of 1 mm.

FIGS. 5A and 5B illustrate principal stresses in an object in accordance with embodiments of the present technology. An analytical model is derived for the spherical stone and is validated against a previously employed numerical model. In addition, the inventors use the numerical model to evaluate the dependence of the results on stone geometry and composition. Both spherical and nonspherical geometries may be representative of actual kidney stones, although in clinical practice, the shape of an individual's stone can only be estimated from computed tomography with a resolution on the order of 1 mm. The material properties of urinary stones of different types have been characterized, although clinically the composition is usually unknown at the time of the procedure, thus the inventors evaluate these over their natural range. These results are used to describe the maximum principal stresses occurring in the stones as a function of frequency of ultrasound and different properties of the body stone.

A. Analytical Description

Below is an analytical description of elastic waves in a spherical stone in a liquid caused by an axisymmetric acoustic beam is derived. We consider the continuous wave (CW) case, and physical quantities $\tilde{F}(r,t)$ (e.g., acoustic pressure $\tilde{p}$, stress components $\tilde{T}_{ij}$, particle displacement $\tilde{u}$, etc.) depend on time sinusoidally: $\tilde{F}(r,t)=\text{Re}[F(r)\exp(-i\omega t)]$, where F is a complex amplitude of $\tilde{F}$. In the liquid, the wave equation results in the following Helmholtz equation:

$$\Delta p + k^2 p = 0. \qquad (1)$$

Here p is the complex amplitude of the acoustic pressure, $$k = \frac{\omega}{c_0}$$

is the wavenumber, $\omega$ is angular frequency, and $c_0$ is the speed of sound in the liquid. According to the equation of motion, for the mentioned time dependence $\sim e^{-i\omega t}$, the particle displacement complex amplitude u in the liquid is expressed as follows:

$$u = \frac{1}{\rho_0 c_0^2 k^2} \nabla p, \quad (2)$$

where $\rho_0$ is the liquid density.

The motion of the solid material (inside the sphere) is convenient to describe using the particle displacement vector u. In the general case it can be represented by the scalar and vector potentials $\Phi$ and A:

$$u = -\nabla\Phi + \nabla \times A \quad (3)$$

The scalar and vector potentials $\Phi$ and A describe the longitudinal and shear waves, correspondingly, and as such are governed by the following Helmholtz equations:

$$\Delta\Phi + k_l^2 \Phi = 0, \quad (4)$$

$$\Delta A + k_t^2 A = 0. \quad (5)$$

Here $$k_l = \frac{\omega}{c_l} \text{ and } k_t = \frac{\omega}{c_t}$$

are the wavenumbers for the longitudinal and shear waves. The corresponding wave velocities $c_l$ and $c_t$ are expressed as follows:

$$c_l = \sqrt{\frac{(\lambda + 2\mu)}{\rho_*}}, c_t = \sqrt{\frac{\mu}{\rho_*}},$$

where $\lambda$ and $\mu$ are the Lame constants, $\rho_*$ is the density of the sphere material. According to Hooke's law, the mechanical stress tensor is expressed through the displacement vector $u = (u_1, u_2, u_3)$:

$$T_{ij} = \lambda \delta_{ij} \nabla \cdot u + \mu \left( \frac{\partial u_i}{\partial x_j} + \frac{\partial u_j}{\partial x_i} \right), \quad (6)$$

where $\delta_{ij}$ is the Kronecker delta.

Let an axisymmetric beam with its axis directed along the z-axis be scattered from an elastic sphere in a liquid. Let the center of the sphere be positioned at the origin of the coordinate system. In such a case it is convenient to use spherical coordinates:

$$p_i = \Sigma_{n=0}^\infty Q_n P_n(\cos\theta) j_n(kr), \quad (7)$$

where r is radial distance (distance to origin, i.e., the stone center), $\theta$ is polar angle (angle with respect to axis z-axis), $P_n(\cdot)$ and $j_n(\cdot)$ are the Legendre polynomials and spherical Bessel functions, correspondingly, and the coefficients $Q_n$ describe the structure of the axisymmetric incident beam. For instance, in the case of a plane incident wave propagating along the z axis, $p_i = p_0 \exp(ikz)$, $$Q_n^{(plane\,wave)} = p_0 i^n (2n+1). \quad (8)$$

Another case is a quasi-Gaussian beam focused on the center of the scatterer. The expression for $Q_n$ in such a case can also be presented analytically.

The scattered wave in fluid will be of the form $$p_s = \sum_{n=0}^\infty Q_n c_n h_n^{(1)}(kr) P_n(\cos\theta), \quad (9)$$

where $h_n^{(1)}(\cdot)$ are the spherical Hankel functions of the first kind, and $c_n$ are coefficients that depend on sphere diameter and acoustic properties of the liquid and solid materials.

Because the incident acoustic beam has an axially symmetric structure, there is no dependence on the azimuthal angle $\varphi$ (angle of rotation around the z-axis). Therefore, there is no displacement tangential to the direction of rotation ($u_\varphi = 0$). The two other components of the vortical part of the displacement vector are $$(\nabla \times A)_r = \frac{\left[ \frac{\partial (A_\varphi \sin\theta)}{\partial \theta} - \frac{\partial A_\theta}{\partial \varphi} \right]}{(r \sin\theta)}$$

and $$(\nabla \times A)_\theta = \frac{\left[ \frac{\left(\frac{\partial A_r}{\partial \varphi}\right)}{\sin\theta} - \partial(rA_\varphi) \right]}{r}.$$

Because $$\frac{\partial A_r}{\partial \varphi} = \partial A_\theta$$

$$\frac{\partial}{\partial \varphi} = 0,$$

only the azimuthal component $A_\varphi$ is needed, i.e., the pair of functions $\Phi$ and $A_\varphi$ fully describe the displacement field. These potentials can be expressed in the following form:[21, 24]

$$\Phi = \sum_{n=0}^\infty a_n P_n(\cos\theta) j_n(k_l r), \quad (10)$$

$$A_\varphi = \sum_{n=0}^\infty b_n j_n(k_t r) \frac{dP_n(\cos\theta)}{d\theta}. \quad (11)$$

Here $a_n$ and $b_n$ are coefficients and, similar to $c_n$, depend on the sphere diameter and acoustic properties of the media.

Because previous publications solving the problem of acoustic wave scattering from an elastic sphere do not describe the stress and displacement fields inside the sphere, the corresponding expressions are derived here. Let us introduce the following notations for the spherical Bessel functions arguments: $\xi = k_l r$, $\eta = k_t r$, and $\varsigma = kr$. According to Eqs. (7) and (9), the complex amplitude of the total pressure $p = p_i + p_s$ has the following form:

$$p = \Sigma_{n=0}^\infty Q_n [j_n(\varsigma) + c_n h_n^{(1)}(\varsigma)] P_n(\cos\theta), \quad (12)$$

The stress tensor components in the spherical coordinates are expressed by the following equations, which follow from Eqs. (3) and (6):

$$T_{rr} = \sum_{n=0}^\infty \left\{ \hat{a}_n [v j_n(\xi) - j_n''(\xi)] + \hat{b}_n n(n+1) \left[ \frac{j_n(\eta)}{\eta^2} - \frac{j_n'(\eta)}{\eta} \right] \right\} P_n(\cos\theta), \quad (13)$$

-continued $$T_{\theta\theta} = \sum_{n=0}^{\infty} \left\{ \hat{a}_n \left[ v j_n(\xi) + n(n+1)\frac{j_n(\xi)}{\xi^2} - \frac{j_n'(\xi)}{\xi} \right] + \hat{b}_n n(n+1)\frac{j_n'(\eta)}{\eta} \right\} \quad (14)$$

$$P_n(\cos\theta) + \sum_{n=0}^{\infty} \left\{ \hat{a}_n \frac{j_n(\xi)}{\xi^2} + \hat{b}_n \left[ \frac{j_n(\eta)}{\eta^2} + \frac{j_n'(\eta)}{\eta} \right] \right\} \frac{\cos\theta}{\sin\theta} \frac{dP_n(\cos\theta)}{d\theta},$$

$$T_{\theta\theta} =$$

$$\sum_{n=0}^{\infty} \left\{ \hat{a}_n \left[ v j_n(\xi) + n(n+1)\frac{j_n(\xi)}{\xi^2} - \frac{j_n'(\xi)}{\xi} \right] + \hat{b}_n n(n+1)\frac{j_n'(\eta)}{\eta} \right\} P_n(\cos\theta) +$$

$$\sum_{n=0}^{\infty} \left\{ \hat{a}_n \frac{j_n(\xi)}{\xi^2} + \hat{b}_n \left[ \frac{j_n(\eta)}{\eta^2} + \frac{j_n'(\eta)}{\eta} \right] \right\} \frac{\cos\theta}{\sin\theta} \frac{dP_n(\cos\theta)}{d\theta},$$

$$T_{\varphi\varphi} = \sum_{n=0}^{\infty} \left\{ \hat{a}_n \left[ v j_n(\xi) - \frac{j_n'(\xi)}{\xi} \right] - \hat{b}_n n(n+1)\frac{j_n(\eta)}{\eta^2} \right\} P_n(\cos\theta) - \quad (15)$$

$$\sum_{n=0}^{\infty} \left\{ \hat{a}_n \frac{j_n(\xi)}{\xi^2} + \hat{b}_n \left[ \frac{j_n(\eta)}{\eta^2} + \frac{j_n'(\eta)}{\eta} \right] \right\} \frac{\cos\theta}{\sin\theta} \frac{dP_n(\cos\theta)}{d\theta},$$

$$T_{\varphi\varphi} = \sum_{n=0}^{\infty} \left\{ \hat{a}_n \left[ v j_n(\xi) - \frac{j_n'(\xi)}{\xi} \right] - \hat{b}_n n(n+1)\frac{j_n(\eta)}{\eta^2} \right\} P_n(\cos\theta) -$$

$$\sum_{n=0}^{\infty} \left\{ \hat{a}_n \frac{j_n(\xi)}{\xi^2} + \hat{b}_n \left[ \frac{j_n(\eta)}{\eta^2} + \frac{j_n'(\eta)}{\eta} \right] \right\} \frac{\cos\theta}{\sin\theta} \frac{dP_n(\cos\theta)}{d\theta},$$

$$T_{r\theta} = \sum_{n=0}^{\infty} \quad (16)$$

$$\left\{ \hat{a}_n \left[ \frac{j_n(\xi)}{\xi^2} - \frac{j_n'(\xi)}{\xi} \right] - \frac{1}{2}\hat{b}_n \left[ j_n''(\eta) + (n-1)(n+2)\frac{j_n(\eta)}{\eta^2} \right] \right\} \frac{dP_n(\cos\theta)}{d\theta}.$$

Here $\hat{a}_n = 2\mu k_t^2 a_n$, $\hat{b}_n = 2\mu k_t^2 b_n$, the prime indicates the derivative over the function argument, and the second derivative of the spherical Bessel function is expresses as $$j_n''(\xi) = \left[ \frac{n(n+1)}{\xi^2} - 1 \right] j_n(\xi) - \frac{2 j_n'(\xi)}{\xi}. \text{ Also, } v = \frac{\lambda}{(2\mu)} = \frac{\sigma}{(1-2\sigma)}$$

is an auxiliary constant, where $$\sigma = 0.5 \frac{(c_l^2 - 2c_t^2)}{(c_l^2 - c_t^2)}$$

is Poisson's ratio.

The particle displacement components in the liquid, according to Eqs. (2) and (12), are expressed as follows:

$$u_r = \sum_{n=0}^{\infty} \frac{Q_n}{k\rho_0 c_0^2} \left[ j_n'(\varsigma) + c_n h_n^{(1)'}(\varsigma) \right] P_n(\cos\theta), \quad (17)$$

$$u_\theta = \sum_{n=0}^{\infty} \frac{Q_n}{k\rho_0 c_0^2} \left[ \frac{j_n(\varsigma)}{\varsigma} + c_n \frac{h_n^{(1)}(\varsigma)}{\varsigma} \right] \frac{dP_n(\cos\theta)}{d\theta}. \quad (18)$$

In the sphere, the corresponding expressions follow from Eqs. (3), (10), and (11):

$$u_r = -\sum_{n=0}^{\infty} \left\{ k_l a_n j_n'(\xi) + k_t b_n n(n+1)\frac{j_n(\eta)}{\eta} \right\} P_n(\cos\theta), \quad (19)$$

$$u_\theta = -\sum_{n=0}^{\infty} \left\{ k_l a_n \frac{j_n(\xi)}{\xi} + k_t b_n \left[ \frac{j_n(\eta)}{\eta} + j_n'(\eta) \right] \right\} \frac{dP_n(\cos\theta)}{d\theta}. \quad (20)$$

Note that the related axial and lateral components of the particle displacement, $u_\parallel$ and $u_\perp$, are expressed through the components $u_r$ and $u_\theta$ as follows:

$$u_\parallel = u_r \cos\theta - u_\theta \sin\theta \quad (21)$$

$$u_\perp = u_r \sin\theta + u_\theta \cos\theta. \quad (22)$$

The expansions' coefficients $a_n$, $b_n$, and $c_n$ are derived from the boundary conditions on the surface of the sphere (r=a), which are continuity of the normal stress $p=-T_{rr}$, absence of the tangential stress $T_{r\theta}=0$, and continuity of the normal component of the displacement $u_r$. The corresponding expressions can be represented in the following form:

$$\hat{a}_n = \beta_n W_n, \quad (23)$$

$$\hat{b}_n = 2\alpha_n W_n, \quad (24)$$

$$c_n = \frac{-\Gamma_n j_n(ka) + j_n'(ka)}{\Gamma_n h_n^{(1)}(ka) - h_n^{(1)'}(ka)}, \quad (25)$$

where the following auxiliary notations are used:

$$\Gamma_n = \frac{\rho_0 c_0}{2\rho_* c_t} \frac{\beta_n \gamma_n + \alpha_n \delta_n}{\beta_n \varepsilon_n + \alpha_n \chi_n}, \quad (26)$$

$$W_n = \frac{Q_n}{\beta_n \varepsilon_n + \alpha_n \chi_n} \frac{j_n(ka) h_n^{(1)'}(ka) - j_n'(ka) h_n^{(1)}(ka)}{\Gamma_n h_n^{(1)}(ka) - h_n^{(1)'}(ka)}, \quad (27)$$

$$\alpha_n = \frac{j_n(k_l a)}{(k_l a)^2} - \frac{j_n'(k_l a)}{k_l a}, \quad (28)$$

$$\beta_n = j_n''(k_t a) + (n-1)(n+2)\frac{j_n(k_t a)}{(k_t a)^2}, \quad (29)$$

$$\gamma_n = \frac{c_l}{c_t} j_n'(k_l a), \quad (30)$$

$$\delta_n = 2n(n+1)\frac{j_n(k_t a)}{k_t a}, \quad (31)$$

$$\varepsilon_n = \frac{\sigma}{1-2\sigma} j_n(k_l a) - j_n''(k_l a), \quad (32)$$

$$\chi_n = 2n(n+1)\left[ \frac{j_n(k_t a)}{(k_t a)^2} - \frac{j_n'(k_t a)}{k_t a} \right]. \quad (33)$$

Note also that $$a_n = \frac{\hat{a}_n}{2\rho_* \omega^2} \frac{c_l^2}{c_t^2}, \quad (34)$$

$$b_n = \frac{\hat{b}_n}{2\rho_* \omega^2}. \quad (35)$$

Equations (12)-(35) provide the exact analytical solution of the considered problem. In lithotripsy, the fracture of stones is the primary effect of interest. The maximum principal stress and peak elastic energy in the stone can be used as parameters that indicate the possibility to initiate appearance and growth of cracks. To find these values, it is necessary to express the time-dependent stress tensor components:

$$\tilde{T}_{ij}(r,\theta,t) = \text{Re}[T_{ij}(r,\theta)\exp(-i\omega t)]. \quad (36)$$

The principal stress components can be expressed as follows:

$$T_{I,II} = \frac{\tilde{T}_{rr} + \tilde{T}_{\theta\theta}}{2} \pm \sqrt{\left(\frac{\tilde{T}_{rr} - \tilde{T}_{\theta\theta}}{2}\right)^2 + \tilde{T}_{r\theta}^2}, \quad (37)$$

$$T_{III} = \tilde{T}_{\varphi\varphi}. \quad (38)$$

From here, the time-dependent maximum principal stress in different points in the stone can be calculated:

$$T \max(T_I, T_{II}, T_{III})_{max}. \quad (39)$$

Elastic potential energy distribution in the stone can be characterized by the free energy density, which is expressed through the stress tensor:

$$E = \frac{1}{4\mu}\tilde{T}_{ik}\tilde{T}_{ik} - \left(\frac{1}{12\mu} - \frac{1}{18K}\right)\tilde{T}_{ll}^2. \quad (40)$$

Here $$K = \lambda + \frac{2\mu}{3}$$

is the bulk modulus, $\tilde{T}_{ik}\tilde{T}_{ik} = \tilde{T}_{rr}^2 + \tilde{T}_{\theta\theta}^2 + \tilde{T}_{\varphi\varphi}^2 + 2\tilde{T}_{r\theta}^2$, and $\tilde{T}_{ll} = \tilde{T}_{rr} + \tilde{T}_{\theta\theta} + \tilde{T}_{\varphi\varphi}$.

Note that for stones that are not too large in comparison with the wavelength, the greatest stresses and free energy density are achieved near the center of the stone. In the center of the sphere, expressions for the maximum principal stress and free energy density are simplified and do not require the use of infinite sums and special functions, since at r=0 only the terms of Eqs. (13)-(16) corresponding to the indices n=0 and n=2 are nonzero.

B. Finite-Difference Model

The analytical solution described above is applicable only to the case of a uniform spherical stone. For stones of arbitrary shape and structure, the analysis can be performed using direct numerical modeling, e.g., in finite differences. In the axisymmetric case it is convenient to use cylindrical coordinates $(r_\perp, z, \varphi)$, where $r_\perp$ is the transverse coordinate. Because of the axial symmetry, the velocity vector $$\tilde{v} = \frac{\partial \tilde{u}}{\partial t}$$

has only two components: radial, $\tilde{v}_{r_\perp}$, and axial, $\tilde{v}_z$, and the stress tensor has only four nonzero components: $\tilde{T}_{r_\perp r_\perp}$, $\tilde{T}_{zz}$, $\tilde{T}_{\varphi\varphi}$, and $\tilde{T}_{r_\perp z}$. Here, as earlier, the tilde indicates the full time-dependent quantity versus the complex amplitudes of the quantity. These six functions describing the mechanical field are governed by the following evolution equations:

$$\frac{\partial \tilde{v}_{r_\perp}}{\partial t} = \frac{1}{\rho}\left\{\frac{1}{r_\perp}\frac{\partial[r_\perp(\tilde{T}_{r_\perp r_\perp} - \tilde{T}_{\varphi\varphi})]}{\partial r_\perp} + \frac{\partial \tilde{T}_{r_\perp z}}{\partial z} + \frac{\partial \tilde{T}_{\varphi\varphi}}{\partial r_\perp}\right\}, \quad (41)$$

$$\frac{\partial \tilde{v}_z}{\partial t} = \frac{1}{\rho}\left[\frac{1}{r_\perp}\frac{\partial(r_\perp \tilde{T}_{r_\perp z})}{\partial r_\perp} + \frac{\partial \tilde{T}_{zz}}{\partial z}\right], \quad (42)$$

$$\frac{\partial \tilde{T}_{r_\perp r_\perp}}{\partial t} = \lambda\left[\frac{1}{r_\perp}\frac{\partial(r_\perp \tilde{v}_r)}{\partial r_\perp} + \frac{\partial \tilde{v}_z}{\partial z}\right] + 2\mu\frac{\partial \tilde{v}_{r_\perp}}{\partial r_\perp}, \quad (43)$$

$$\frac{\partial \tilde{T}_{zz}}{\partial t} = \lambda\frac{1}{r_\perp}\frac{\partial(r_\perp \tilde{v}_{r_\perp})}{\partial r_\perp} + (\lambda + 2\mu)\frac{\partial \tilde{v}_z}{\partial z}, \quad (44)$$

$$\frac{\partial \tilde{T}_{\varphi\varphi}}{\partial t} = \lambda\frac{\partial \tilde{v}_z}{\partial z} + (\lambda + 2\mu)\frac{1}{r_\perp}\frac{\partial(r_\perp \tilde{v}_{r_\perp})}{\partial r_\perp} - 2\mu\frac{\partial \tilde{v}_{r_\perp}}{\partial r_\perp}, \quad (45)$$

$$\frac{\partial \tilde{T}_{r_\perp z}}{\partial t} = \mu\left(\frac{\partial \tilde{v}_z}{\partial r_\perp} + \frac{\partial \tilde{v}_{r_\perp}}{\partial z}\right). \quad (46)$$

In the numerical modeling, it is convenient to consider the liquid and stone as one inhomogeneous medium, whose parameters $\rho$, $\lambda$, and $\mu$ are functions of the coordinate locations. In the liquid, $\rho = \rho_0$, $\lambda = \rho_0 c_0^2$, and $\mu = 0$. In the stone, $\rho = \rho_*$, $\lambda = \rho_*(c_l^2 - 2c_t^2)$, and $\mu = \rho_* c_t^2$. When such parameters are used in Eqs. (41)-(46), the boundary conditions at the stone surface are satisfied automatically.

To solve the system of Eqs. (41)-(46) numerically, the partial differential equations are discretized using a central differencing scheme with staggered grids in both space and time. To account for an incident acoustic wave, a proper boundary condition is set at the calculation box boundary. The typical spatial grid step for the coordinates was 50 μm, and the temporal step was 10 ns, which was sufficient to maintain stability and accuracy. A matched layer (PML) of 1.5-mm thickness is placed at the boundary of the calculation region of 50×50 mm size.

Similar to the analytical approach, the results of numerical modeling are analyzed using maximum principal stress and free energy density. The principal stress components are expressed similar to Eqs. (37):

$$T_{I,II} = \frac{\tilde{T}_{r_\perp r_\perp} + \tilde{T}_{zz}}{2} \pm \sqrt{\left(\frac{\tilde{T}_{r_\perp r_\perp} - \tilde{T}_{zz}}{2}\right)^2 + \tilde{T}_{r_\perp z}^2}, \quad (47)$$

and the third principal stress is described by Eq. (38), i.e., $T_{III} = \tilde{T}_{\varphi\varphi}$. The maximum principal stress then is calculated according to Eq. (39). The free energy density has the form of Eq. (40), in which $\tilde{T}_{ik}\tilde{T}_{ik} = \tilde{T}_{r_\perp r_\perp}^2 + \tilde{T}_{zz}^2 + \tilde{T}_{\varphi\varphi}^2 + 2\tilde{T}_{r_\perp z}^2$, and $\tilde{T}_{ll} = \tilde{T}_{r_\perp r_\perp} + \tilde{T}_{zz} + \tilde{T}_{\varphi\varphi}$.

In lithotripsy, the formation of cracks under the action of a tensile load is of interest; therefore, it is convenient to use the maximum principal stress $T_{max}$ as a parameter. As the inventors' interest is the effect of the wave frequency on $T_{max}$ and since the maximum principal stress also depends on time, it makes sense to use the peak value of the maximum stress in time, $$\max_{time}(T_{max}),$$

as an indicator of the impact at the selected point of the stone, and to characterize the possibility of stone fragmentation, use the largest value within the entire stone, $$\max_{space}\left[\max_{time}(T_{max})\right].$$

This value depends on the frequency of the wave and the size of the stone by means of a dimensionless frequency ka. Here data are presented versus ka for the sounds speed in the surrounding water.

C. Material Properties

To relate the study to lithotripsy, the properties of the sphere are chosen to represent natural kidney stones and commonly used artificial stone models for testing that are shown in Table 1 below. For example, the liquid can be water with the density $\rho_0=1000$ kg/m$^3$ and the speed of sound $c_0=1500$ m/s, which is reasonable for urine or tissue that surrounds the stone. The shape of the stone was spherical for the analytical theory, and spherical, cylindrical, or biconical (with diameter equal to the length) for the finite-difference modeling.

TABLE 1

Properties Used in the Simulation to Model Renal Calculi Composition

| MATERIAL* | $\rho$, kg/m$^3$ | $c_l$, m/s | $c_t$, m/s |
|---|---|---|---|
| Water | 1000 | 1500 | 0 |
| COM | 1823 | 4476 | 2247 |
| COD | 1875 | 2687 | 1344 |

*COM = calcium oxalate monohydrate; COD = calcium oxalate dihydrate

D. Experiments

The rate of stone breakage by low (390 kHz) and high (830 kHz) frequency BWL in stones ranging in size of 1-3 mm and 3-5 mm was evaluated in water bath. In some embodiments, the 830-kHz transducer was used because it had the same beamwidth (>5 mm) of the 390-kHz transducer to be effective on stones 5-mm and smaller and a frequency predicted to be effective on stones 1 mm and larger; the 650-kHz transducer used above had a narrower beamwidth only appropriate for the 2.6-mm stone. Each set of stones were matched by size and exposed to either the low frequency or high frequency burst. In addition, a third set of 3-5 mm stones was exposed to a combination of low frequency burst followed by a high frequency burst (Mixed Set).

Stones: All stones were predominately COM (>95% as measured by infrared spectroscopy), and all were hydrated for more than one week before the experiment. All stones were weighed wet before use. COM stones are the most common type, and other stone compositions were investigated too.

Setup: The stone was held in a water-filled depression in a tissue mimicking phantom simulating a calyx. The depression was cylindrical with a 5-mm diameter×10-mm deep well with a pointed bottom that ensured stone and fragments stayed at the focus. The transducer pointed downward at the phantom in a water bath at 50% oxygen saturation. The conditions were chosen to mimic thresholds for cavitation in vivo as measured with the 390-kHz frequency, and exposure conditions for clinical trials with 390-kHz were chosen to avoid formation of a cavitation cloud. The inline ultrasound imaging is used to detect if a cavitation cloud forms, and treatment is then paused. No cavitation clouds were observed in the current experiment with either frequency.

Fragments were removed from the phantom every 2.5 minutes and passed through a 1-mm sieve. The remaining (residual) fragments that did not pass through the sieve were weighed and then passed through a 2-mm sieve. The residual fragments that did not pass through the 2-mm sieve were again weighed. All stones greater than 1 mm were returned to the phantom for more treatment.

Exposure parameters: The BWL therapy was delivered using two separate transducers for the different frequencies, but both had the same beamwidth, which was 6 mm and wider than the maximum dimension of all the stones. The exposure consisted of 6 MPa peak negative pressure, 20-cycle pulse duration, and 10 Hz pulse repetition frequency. This was consistent with the clinical dose taking into consideration tissue attenuation. All stones were exposed for 10 minutes maximum. In the mixed frequency case, the first 2.5-minute exposure was at low frequency and the remaining 7.5-minute exposure was at high frequency.

Analysis: The residual masses were normalized to the initial mass and averaged at each time point for each exposure, sieve size, and stone (set) size. Large stones and small stones were analyzed separately. The rates of comminution were statistically compared in two approaches: interval censored time-to-event data and longitudinal data analysis based on the remaining percentages. Time-to-event data included two approaches: generalized log-rank and a Cox proportional hazard model for interval censored data. The longitudinal data analysis approach was used to predict the probability outcome of complete comminution based on the remaining residual stone masses and were analyzed overall and at each time point. Linear mixed effects models were used with a random intercept for stone level, and another random intercept at the matching level. Time was treated as a categorical variable, for the time trend is nonlinear. The frequency effects were analyzed by comparing the longitudinal mean profiles across different frequencies. All duplicate measures agreed on statistical significance (p-value<0.05), and the highest p-value is presented.

FIG. 6A is a graph of BWL bursts in accordance with embodiments of the present technology. FIG. 6A shows aspects of a BWL waveform. In some embodiments, BWL waveform may be produced, for example, in any of the manners described above in relation to FIGS. 1-3. The BWL waveform includes a number of bursts 501, 502, 503, etc., represented by the letter "N." For example, the number of bursts, N, may represent the number of bursts required to fragment or comminute an object. A burst time period is illustrated for the duration of burst and a rest time period is illustrated between burst 501 and burst 502. Other illustrated bursts may have burst time periods and rest time periods in between them. As such, combining the burst times and the rest times may amount to a time period for producing BWL waveform.

Figure 6B:
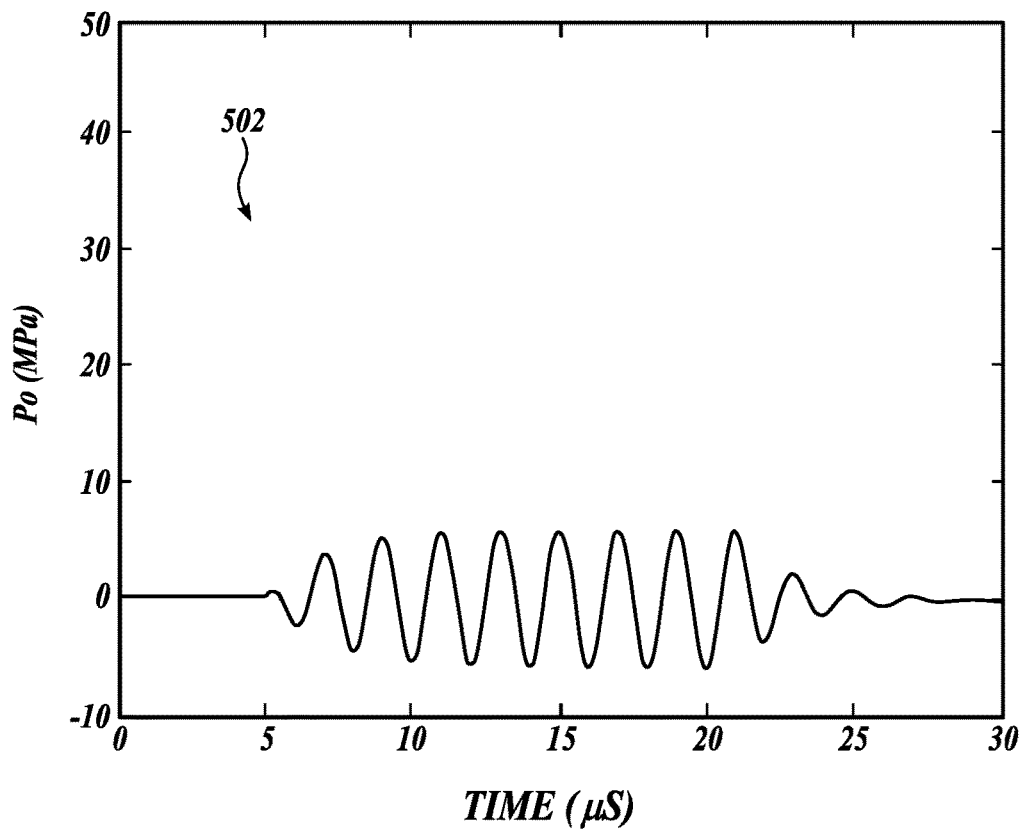
FIG. 6B is a graph of a ultrasound waveforms in an individual BWL burst in accordance with embodiments of the present technology.

FIG. 6B is a graph of ultrasound waveforms in an individual BWL burst in accordance with embodiments of the present technology. FIG. 6B illustrates a close-up view of burst 502 from FIG. 6A. In some embodiments, burst 502 may be produced, for example, in any of the manners described above in relation to FIGS. 1-3. The horizontal axis shows time in μs, and the vertical axis shows the pressure of the ultrasound acoustic field at the focal plane in MPa. The illustrated ultrasound waves are smooth ultrasound waves (e.g., sinusoidal waves). The areas on the left and right sides of burst 502 correspond to the rest times. The illustrated burst 502 includes about 8 cycles, each cycle taking about 2 μs, but other numbers of cycles in a given burst and other frequencies of cycle are also possible.

Figure 6C:
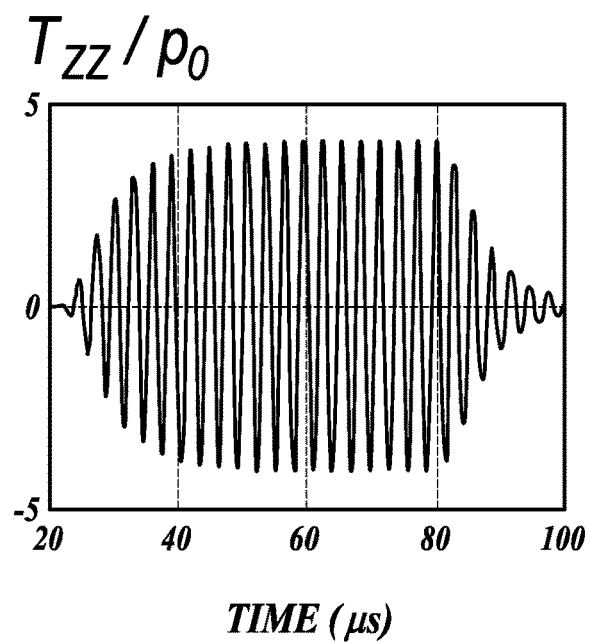
FIG. 6C is a graph of a stress burst waveform in an object in accordance with embodiments of the present technology.

FIG. 6C is a graph of a stress burst waveform in an object in accordance with embodiments of the present technology. The horizontal axis shows time in μs and the vertical axis shows stress burst as a ratio between Tzz (principal stress in z-direction) and p0 (acoustic pressure of the ultrasound). When the frequency of the ultrasound is properly matched to the size of target object (e.g., a body stone), a significant amplification of the acoustic pressure of the BWL waves can be achieved. In the illustrated embodiments, such amplification corresponds to about 4-5 times, and may be already achieved after only 5-6 cycles of the ultrasound waves. In other embodiment, $T_{zz}/p_0$ ratio of 2-3 may already suffice for breaking certain target stones in a body. In the illustrated embodiments, the ultrasound frequency that is suitable for a particular size of the test object is about 340 kHz.

Figure 7:
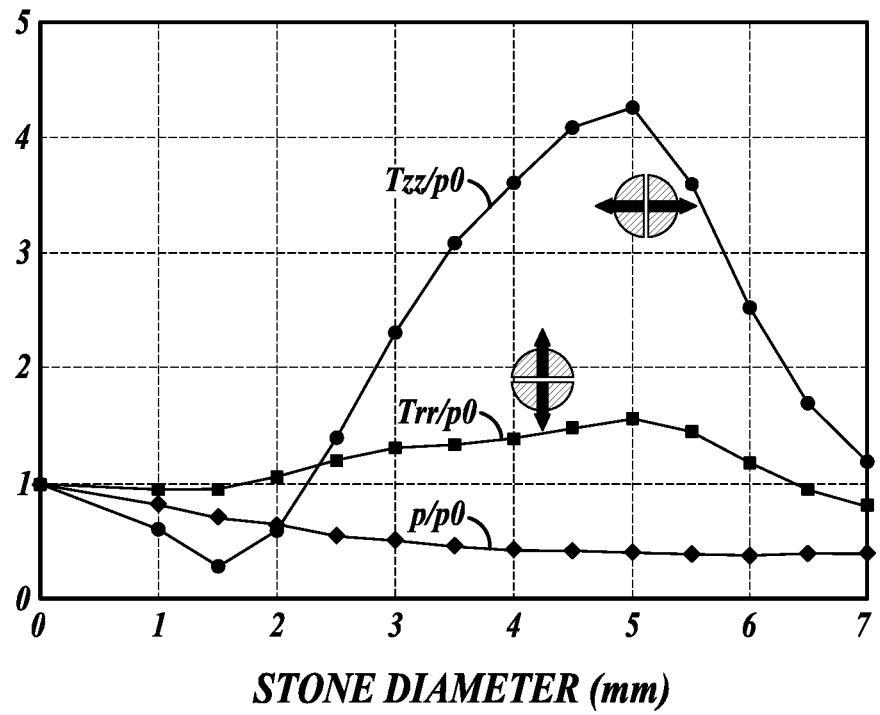
FIG. 7 is a graph of a normalized stress amplitude in an object in accordance with embodiments of the present technology.

FIG. 7 is a graph of a normalized stress amplitude in an object in accordance with embodiments of the present technology. The horizontal axis shows stone diameter in mm, and the vertical axis shows normalized stress amplitude at center of the object. The frequency of the ultrasound is 340 kHz, same as in FIG. 6 above. FIG. 7 demonstrates that the highest principal stress is achieved for a body stone of about 5 mm size. The inventors have found out that a relationship between the most effective frequency of the BWL wave and the diameter of the stone can be described as:

$$\frac{df}{c} \approx Const. \quad (48)$$

where:
d is a diameter of the target object,
f is a frequency of the BWL wave,
c is the shear wave speed (or other representative wave speed) in the target (e.g., body stone), and
Const. is a predetermined constant. The inventors have found that the value of the predetermine constant corresponds to approximately ¾ in many cases, especially when the shear wave speed is used as a representative wave speed in the target. However, values of the "Const." that are different from ¾ are also possible in different embodiments depending on the representative wave speed used in equation (48). For example, the value of Const. is approximately ⅜ when the representative value of c corresponds to the longitudinal wave speed. Other representative value is possible when the representative value of c corresponds to the surface value speed.

Figure 8:
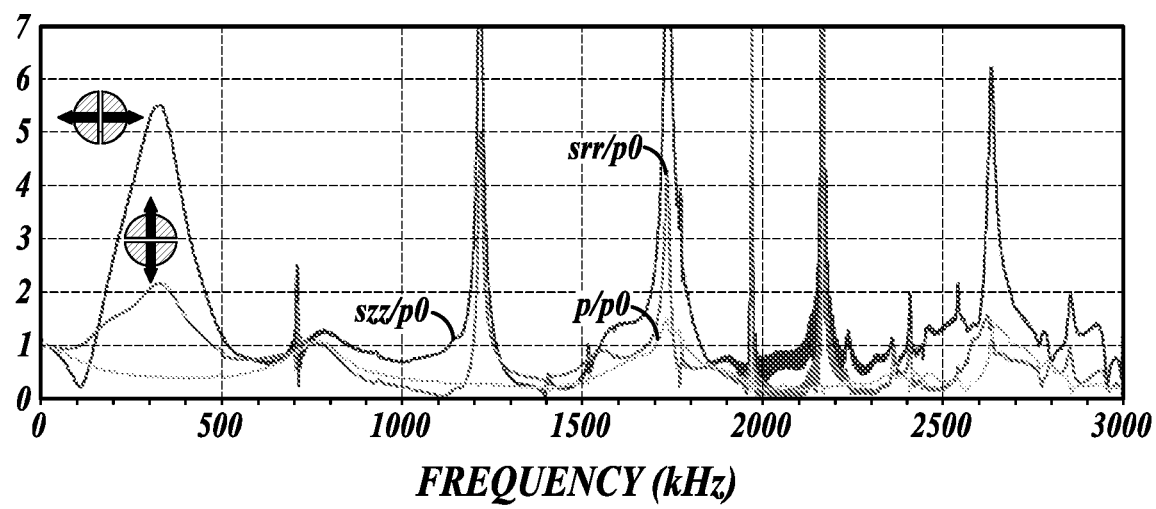
FIG. 8 is a graph of a normalized stress amplitude in an object in accordance with embodiments of the present technology.

FIG. 8 is a graph of a normalized stress amplitude in an object in accordance with embodiments of the present technology. The horizontal axis shows frequency of the BWL ultrasound, and the vertical axis shows amplification of the ultrasound pressure in different planes of the body stone. The size of the tested stone is 5 mm. Here, the ultrasound frequency that is characterized by the highest amplification of the stresses in the target stone corresponds to about 340 kHz, the remaining peaks being the harmonics of the main peak at 340 kHz.

Figure 9:
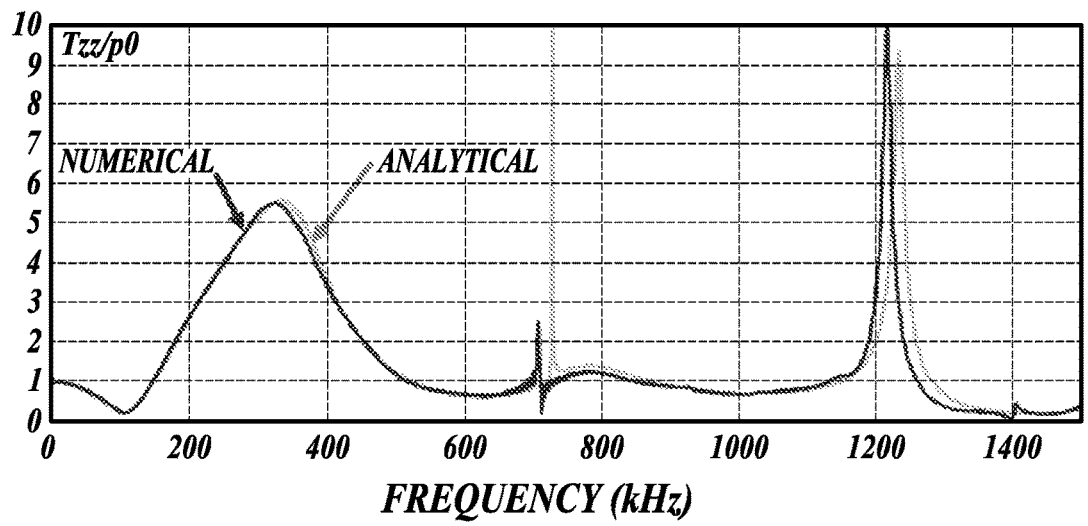
FIG. 9 is a comparison graph of analytically and numerically obtained stress amplitude in an object in accordance with embodiments of the present technology.

FIG. 9 is a comparison graph of analytically and numerically obtained stress amplitude in an object in accordance with embodiments of the present technology. The horizontal axis shows the frequency of the BWL ultrasound in kHz. The vertical axis shows a ratio of the principal stress (Tzz) in the body stone and the pressure of the ultrasound field (p0). The size of the stone is 5 mm, same as with the several examples illustrated above. In general, agreement between the numerical and analytical solution is good, indicating possibility of determining, for example, the frequency of the BWL ultrasound f in the equation 48 based on known size (d) and shear wave speed (c, defined by the material composition of the stone) of the target stone.

Figure 10:
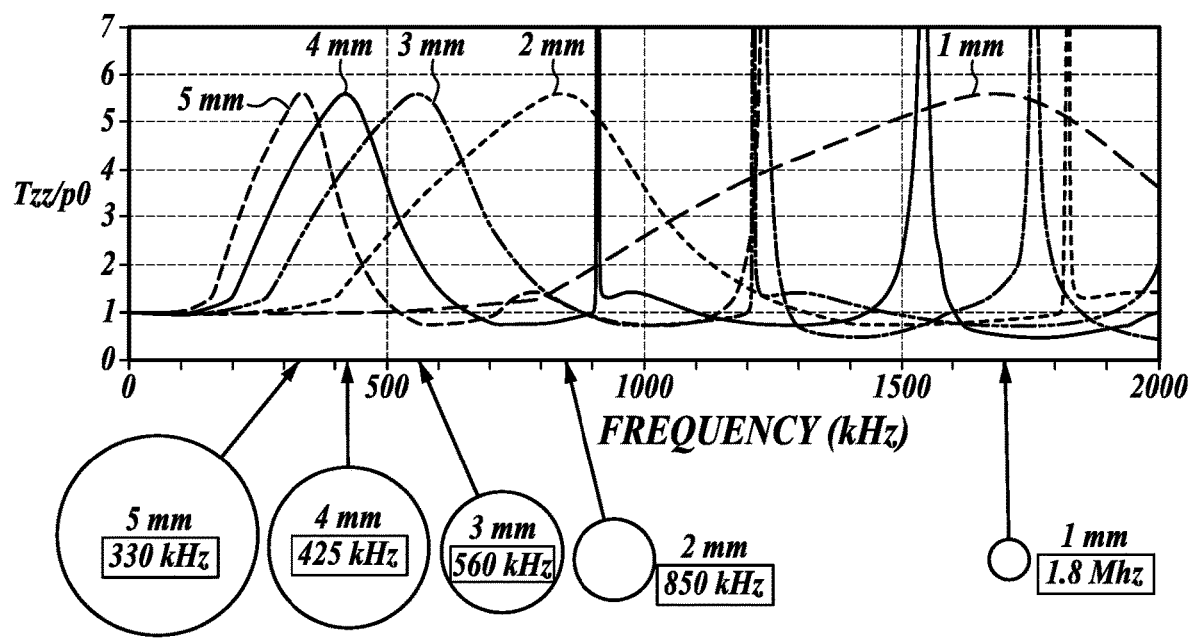
FIG. 10 is a graph of optimal BWL frequency in accordance with embodiments of the present technology.

FIG. 10 is a graph of optimal BWL frequency in accordance with embodiments of the present technology. The horizontal axis shows frequency of the BWL ultrasound in kHz. The vertical axis shows a ratio of the principal stress (Tzz) in the body stone and the pressure of the ultrasound field (p0). The ratio is shown for the stones of different sizes. It can be seen that for the stones ranging from 5 mm to 1 mm, the optimum frequency of the BWL ultrasound ranges from about 330 kHz to about 1.8 MHz. These frequencies are derivable from equation 48 above.

Figure 11:
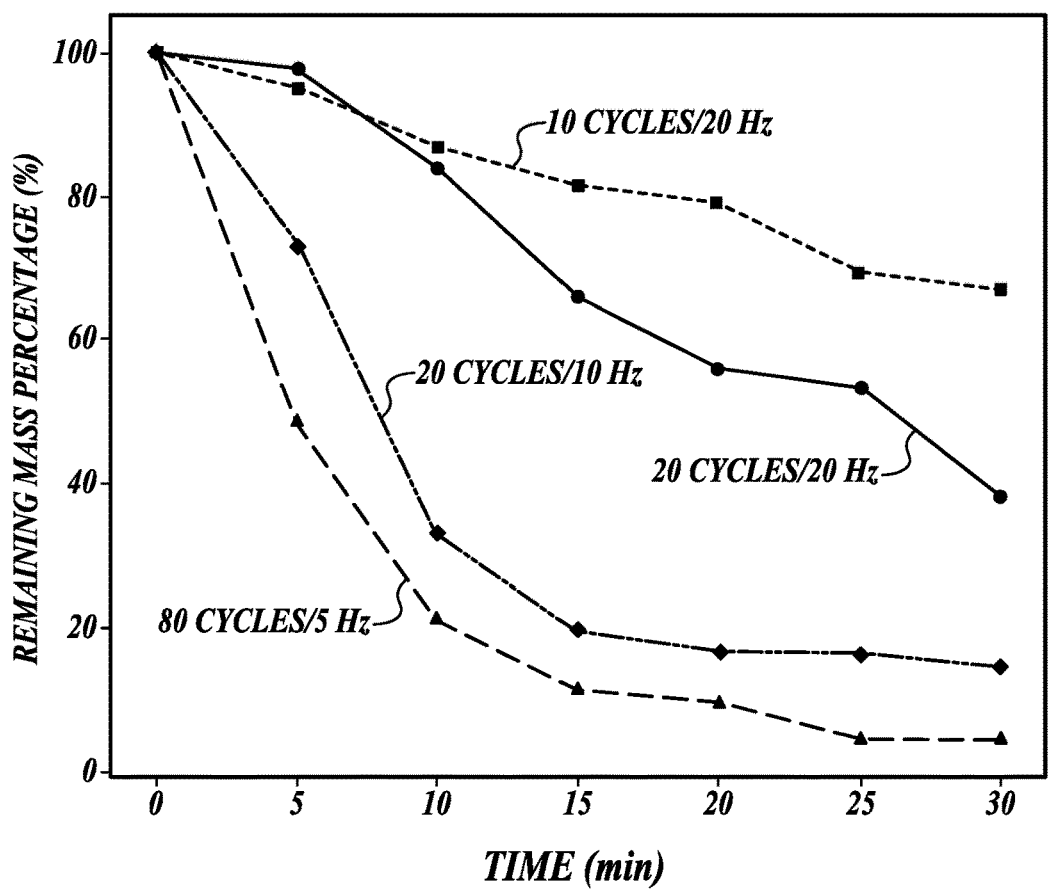
FIG. 11 is a graph of sizes of comminuted stone fragments in accordance with embodiments of the present technology.

FIG. 11 is a graph of sizes of comminuted stone fragments in accordance with embodiments of the present technology. The horizontal axis shows the treatment time in minutes, and the vertical axis shows a percentage of the stone fragments that are 2 mm and larger. The starting size of the human calcium oxalate stones was between 4-7 mm. These stones were exposed in a tissue phantom with a 350 kHz BWL transducer with a −6 dB beamwidth of 6 mm and focal length of 100 mm. Different curves correspond to different numbers of BWL repletion (cycles) and the frequency of the BWL bursts.

The ultrasound treatments were delivered in a water bath that was degassed to 45-50% of saturation. Inline ultrasound imaging was used to target the stone and monitor cavitation activity around the stone. Stones were exposed to 10 different parameter sets at a peak negative pressure of 6.2 MPa in 5-minute intervals up to 30 minutes total. After each period, the remaining mass of fragments>2 mm was measured to determine the time course of comminution of the initial stones. There was a clear trend in results with longer pulses producing improved fragmentation. However, increasing the pulse repetition rate with set pulse duration does not always produce faster comminution. The results suggest that more effective fragmentation may be achieved in BWL by long pulse durations and low pulse repetition frequency (PRF) rather than the opposite approach.

Figure 12:
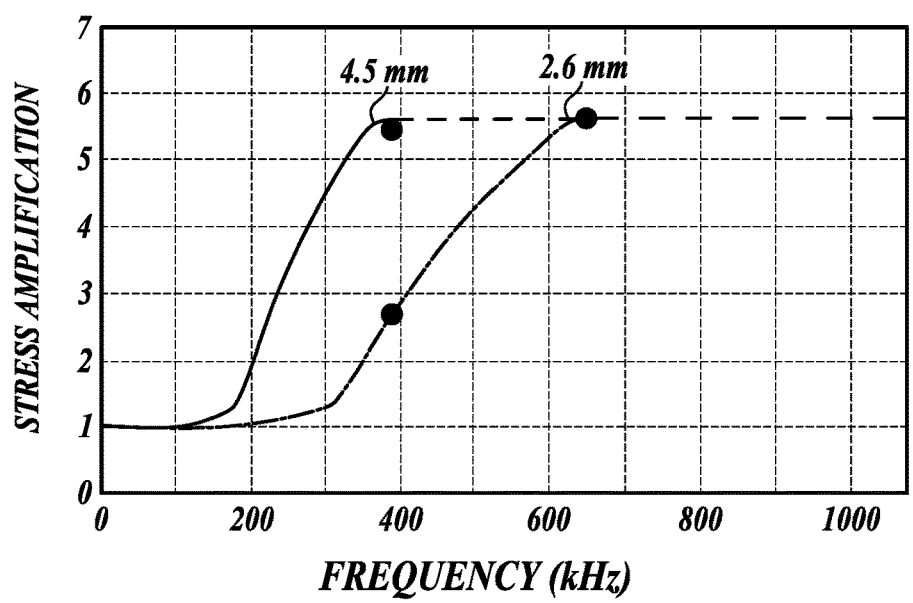
FIG. 12 is a graph of stress amplification in accordance with embodiments of the present technology.

FIG. 12 is a graph of stress amplification in accordance with embodiments of the present technology. The horizontal axis shows a frequency of the BWL waveform in kHz. The vertical axis shows stress amplification ($T_{zz}/p_0$). Therefore, the graph illustrates a peak maximum principal stress within a stone that is normalized to the peak pressure of the applied BWL pulse vs. BWL frequency for two stone sizes. For the 4.5 mm stone, the pressure amplification is more than 5.5 at both 350 kHz and 650 kHz. However, for the smaller 2.6 mm stone (orange line), the amplification is 2.8 at 390 kHz, but is 5.5 at 650 kHz. A dashed line is shown to the right of the peak to reflect that the amplification remains consistent. The plots show a threshold in minimum frequency that must be used to achieve the maximum pressure amplification for a certain stone diameter. Furthermore, the plots indicate that a frequency of about 650 kHz is effective to comminute both the stone having 2.6 mm diameter, as well as the larger stones having diameters in excess of 2.6 mm. Therefore, the above equation 48 may be generalized to define a frequency that is effective for a certain diameter of the target stone as:

$$f \geq Const. \frac{c}{d} \quad (49)$$

Figure 13:
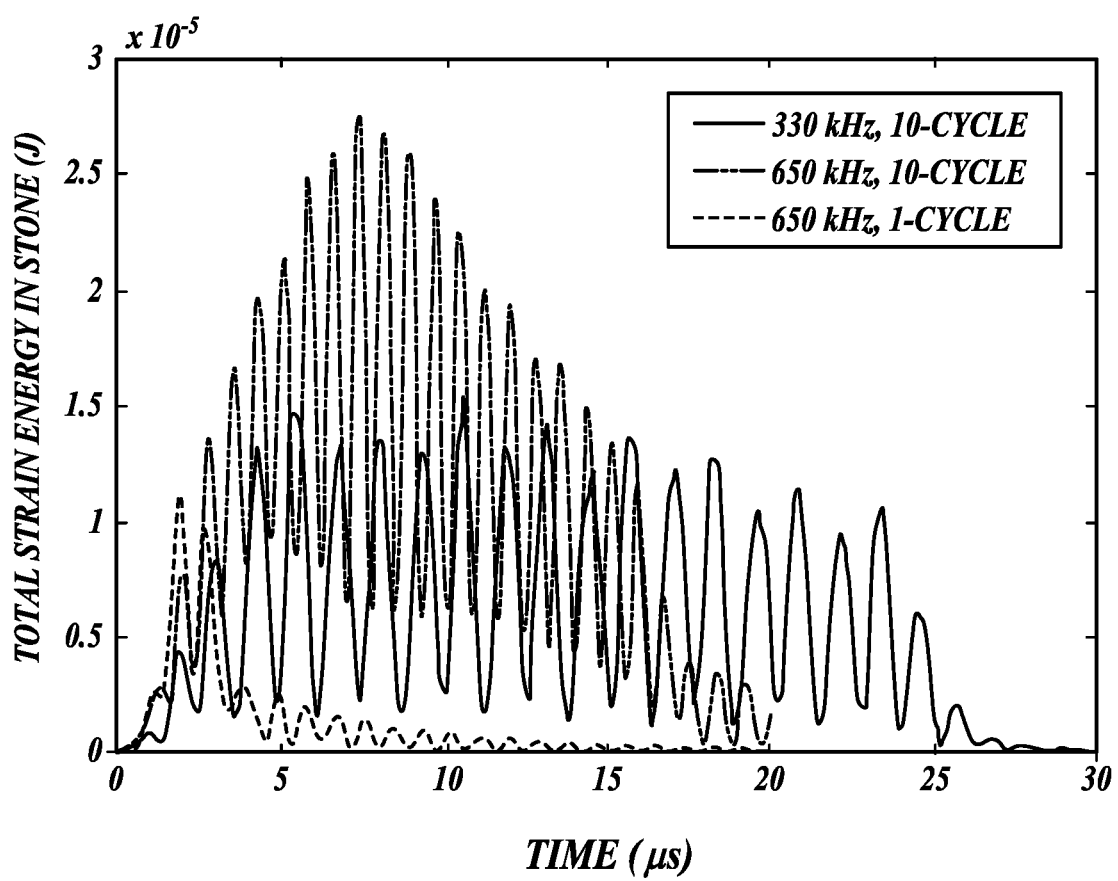
FIG. 13 is a graph of total strain energy in stone in accordance with embodiments of the present technology.

FIG. 13 is a graph of total strain energy in stone in accordance with embodiments of the present technology. As explained above, in many embodiments, especially when the value of "c" corresponds to a speed of the shear wave in the stone, the constant "Const." is about ¾. However, other values are also possible in different embodiments. The horizontal axis shows time in µs, and the vertical axis shows a total strain energy in stone in Joules. The test stone has a diameter of 2.6 mm. FIG. 13 shows the time history of the peak strain energy and damage potential inside the stone at the end of a 1-cycle or 10-cycle, 6-MPa lithotripsy pulse for each frequency. Both indicators support a conclusion that fragmentation is less effective at 390 kHz compared with 650 kHz, in line with the conclusions expressed through equations 48 and 49 above. The graph shows that the total stain energy is nearly double for the higher frequency in this small stone. Similar to the results for the principal stress, the peak strain energy requires at least approximately four cycles before amplification is observed, which is why the amplification is not seen with the single cycle lithotripsy (e.g., shock wave lithotripsy, SWL) pulse. Thus, multiple cycles are required to reach the maximum strain energy for a given a frequency. In other embodiments, at least 5, at least 6, at least 8 or at least 10 cycles are required for an effective stress amplification.

Figure 14A:
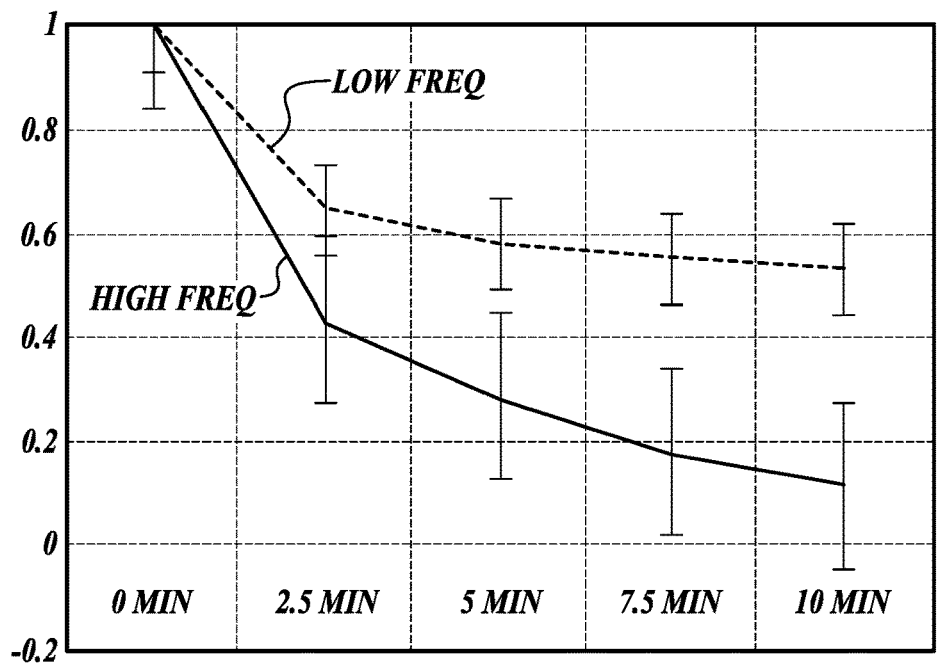
FIGS. 14A-14D are graphs of total strain energy in stone in accordance with embodiments of the present technology.
Figure 14B:
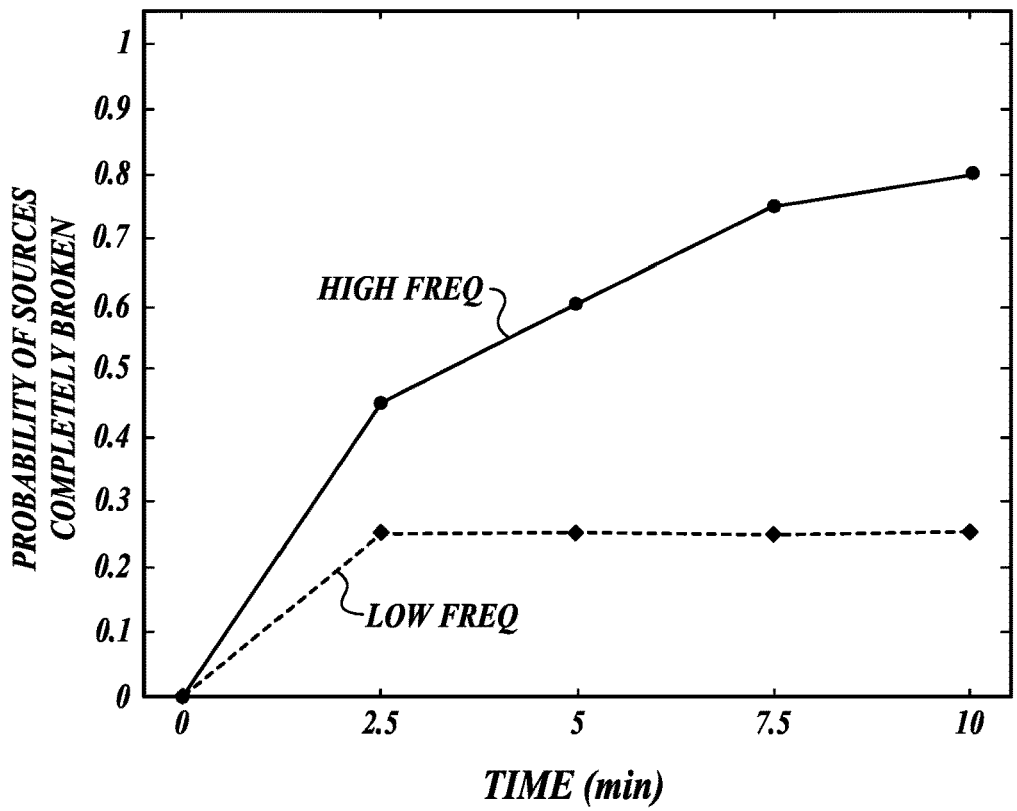

FIGS. 14A-14D are graphs of total strain energy in stone in accordance with embodiments of the present technology. In each case, the horizontal axis shows the duration of the treatment. The vertical axis shows fraction of the residual fragments after a given treatment (FIGS. 14A, 14C and 14D) and a probability of the initial stones being completely broken (FIG. 14B). The low frequency corresponds to 390 kHz BWL ultrasound, and the high frequency corresponds to 830 kHz. After each treatment, the stone fragments are passed through a sieve (either a 1-mm sieve or a 2-mm sieve, as indicated in the graphs), and then returned to the treatment.

FIG. 14A shows the average normalized mass fraction of initially small stone (1-3 mm) fragments being greater than 1 mm remaining at each time point. FIG. 14B shows the probability of the stone being completely broken to smaller than 1 mm fragments. Under both conditions the stones exposed to the higher frequency (830 kHz) BWL burst broke the test stones in the 1-3 mm size range faster and more completely than when exposed to the lower frequency (390 kHz) BWL burst (p=0.0003). The probability curve for the 390-kHz frequency flattened after 2.5 minutes, indicating the stones were not breaking further with additional exposure. In some embodiments, the ultrasound at two different frequencies (e.g., 390 kHz and 830 kHz) may be produced by different ultrasound transducers.

Figure 14C:
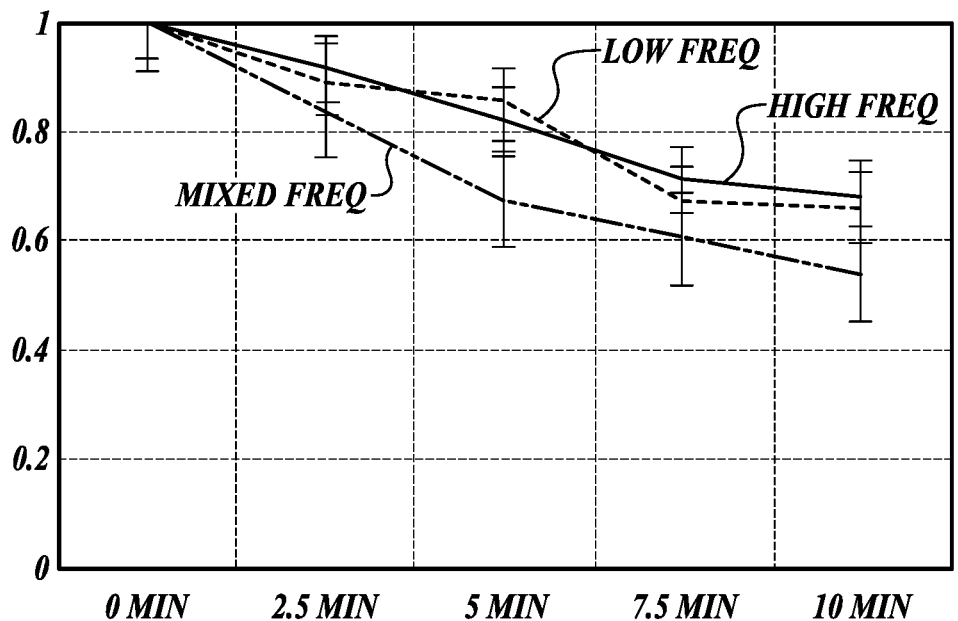
Figure 14D:
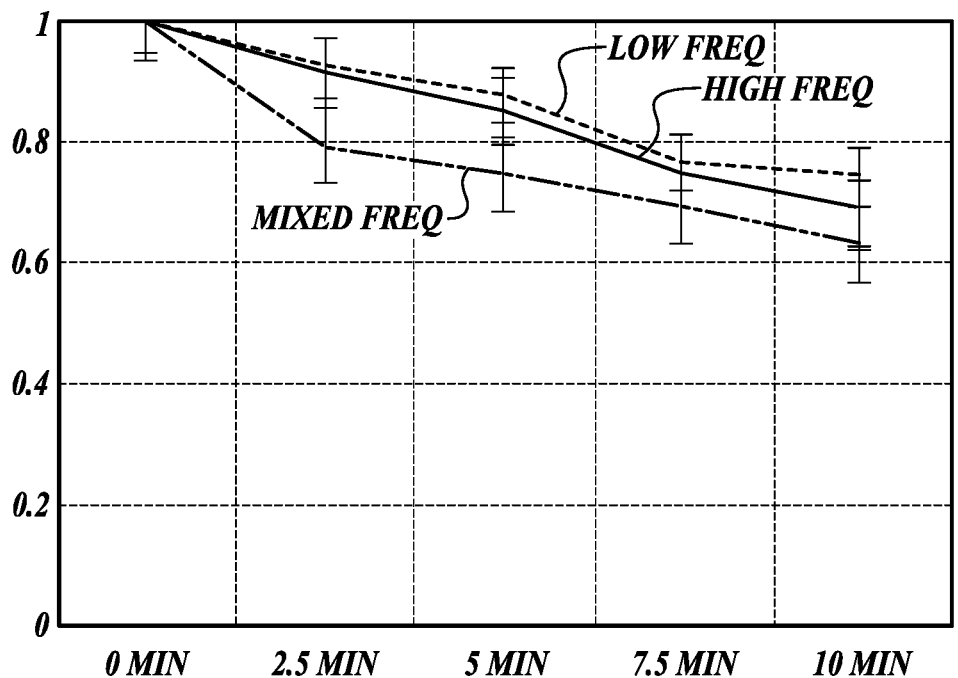

FIG. 14C shows the average normalized mass fraction of initially large stone (3-5 mm) fragments being greater than 2 mm remaining at each time point. FIG. 14D shows the same scenario for the 1 mm fragments. In the illustrated embodiment, there are no statistical differences in rate of fragmentation between large stones exposed to low frequency (390 kHz) BWL, high frequency (830 kHz) BWL, or low frequency (2.5 minutes) followed by high frequency (mixed p=0.2055). The results suggest that though it may not be possible to break a small stone at low frequency, however, to the contrary, it may be possible to use higher frequency over a broad range of stone sizes (1-5 mm), as indicated by the equation 49 above. Stated differently, there seems to be little detriment to using higher frequency, which breaks smaller stones better, to also break larger stones.

Although not statistically significant, there is a trend of improved comminution effectiveness with the mixed frequencies. The statistical results for the fraction of stones is consistent with the longitudinal data analysis. Only one time point (at 5 minutes) was found to be significant, but significance was lost when the model was adjusted for multiplicity.

The terms used in the embodiments of the present disclosure are merely for the purpose of describing specific embodiment, rather than limiting the present disclosure. The terms "a", "an", "the", and "said" in a singular form in the embodiments of the present disclosure and the attached claims are also intended to include plural forms thereof, unless noted otherwise.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Such computers, controllers and data processors may include a non-transitory computer-readable medium with executable instructions. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Where methods are described, the methods may include more, fewer, or other steps. Additionally, steps may be performed in any suitable order. Accordingly, the disclosure can encompass other embodiments not expressly shown or described herein. In the context of this disclosure, the term "about," approximately" and similar means+/−5% of the stated value.

For the purposes of the present disclosure, lists of two or more elements of the form, for example, "at least one of A, B, and C," is intended to mean (A), (B), (C), (A and B), (A and C), (B and C), or (A, B, and C), and further includes all similar permutations when any other quantity of elements is listed.

What is claimed is:

1. A lithotripsy system for comminuting a stone in a body, comprising:
a burst wave lithotripsy (BWL) therapy transducer configured to transmit smooth ultrasound waves within a burst of ultrasound waves toward the stone; and
a controller configured to determine an operating frequency of the ultrasound waves of the therapy transducer;
wherein the operating frequency of the ultrasound waves is determined as:

$$f = Const. \frac{c}{d}$$

where:
d is a diameter of the stone,
f is the frequency of the ultrasound waves,
c is a wave speed in the stone, and
Const. is a predetermined constant.

2. The lithotripsy system of claim 1, wherein the wave speed c is a shear wave speed, and wherein Const. corresponds to ¾.

3. The lithotripsy system of claim 1, wherein the operating frequency is a first operating frequency, wherein the first operating frequency operates to break the stone into fragments of a given size range, wherein the controller is configured to determine a second operating frequency such that the second operating frequency (f2) is determined as:

$$f_2 = Const. \frac{c}{d_2}$$

where:
$d_2$ is a diameter of the fragments, and
$f_2$ is the frequency of the ultrasound waves.

4. The lithotripsy system of claim 3, wherein the therapy transducer is a first therapy transducer capable of generating the first operating frequency, the system comprising a second therapy transducer capable of generating the second operating frequency.

5. The lithotripsy system of claim 3, wherein the second operating frequency is determined based on a target size of the fragments as:

$$f_2 \geq Const. \frac{c}{d_{final}}$$

where:
$d_{final}$ is a final target diameter of the fragments.

6. The lithotripsy system of claim 1, wherein the burst of ultrasound waves of the BWL therapy transducer comprises at least 5 cycles of the ultrasound waves.

7. The lithotripsy system of claim 1, wherein the burst of ultrasound waves of the BWL therapy transducer comprises at least 8 cycles of the ultrasound waves.

8. The lithotripsy system of claim 1, wherein the ultrasound waves of the BWL therapy transducer are transmitted as the bursts of ultrasound waves, wherein the bursts of ultrasound waves are repeated in a frequency of 10 Hz.

9. The lithotripsy system of claim 1, wherein the waves of the BWL therapy transducer are transmitted as bursts of ultrasound waves, wherein the bursts are repeated in a frequency of 20 Hz.

10. The lithotripsy system of claim 1, wherein the burst wave lithotripsy (BWL) therapy transducer generates an acoustic pressure $p_0$ in a focal plane and a principal stress $T_{zz}$ in the stone, and wherein a ratio of $T_{zz}/p_0$ is higher than 2.

11. The lithotripsy system of claim 10, wherein the burst wave lithotripsy (BWL) therapy transducer causes an acoustic pressure $p_0$ in a focal plane and a principal stress $T_{zz}$ in the stone, and wherein a ratio of $T_{zz}/p_0$ is higher than 4.

12. The lithotripsy system of claim 1, wherein the ultrasound waves are sinusoidal waves.

13. A method for comminuting a stone in a body using an ultrasound, comprising:
determining an operating frequency of smooth ultrasound waves of a burst wave lithotripsy (BWL) therapy transducer, wherein the therapy transducer is configured to transmit the ultrasound waves within bursts of ultrasound waves at the operating frequency toward the stone; wherein the operating frequency is determined as:

$$f = Const. \frac{c}{d}$$

where:
d is a diameter of the stone,
f is the frequency of the ultrasound waves,
c is a wave speed in the stone, and
Const. is a predetermined constant; and
transmitting the ultrasound waves at the operating frequency toward the stone.

14. The method of claim 13, wherein the wave speed c is a shear wave speed, and wherein Const. corresponds to ¾.

15. The method of claim 13, wherein the operating frequency is a first operating frequency, wherein the first operating frequency operates to break the stone into fragments of a given size range, wherein a second operating frequency (f2) is determined as:

$$f_2 = Const. \frac{c}{d_2}$$

where:
$d_2$ is a diameter of the fragments, and
$f_2$ is the frequency of the ultrasound waves.

16. The method of claim 15, wherein the therapy transducer is a first therapy transducer capable of generating the first operating frequency, the method comprising generating the second operating frequency by a second therapy transducer.

17. The method of claim 13, wherein the operating frequency of the ultrasound waves ($f_{final}$) is determined based on a target size of stone fragments as:

$$f_{final} \geq Const. \frac{c}{d_{final}}$$

where:
$d_{final}$ is a final target diameter of the fragments.

18. The method of claim 17, wherein entire treatment is executed with the therapy transducer operating at the operating frequency of the ultrasound waves $f_{final}$.

19. The method of claim 13, wherein the therapy transducer generates an acoustic pressure $p_0$ in a focal plane and a principal stress $T_{zz}$ in the stone, and wherein a ratio of $T_{zz}/p_0$ is higher than 2.

20. The method of claim 19, wherein the therapy transducer generates an acoustic pressure $p_0$ in a focal plane and a principal stress $T_{zz}$ in the stone, and wherein a ratio of $T_{zz}/p_0$ is higher than 4.

21. The method of claim 13, wherein the ultrasound waves are sinusoidal waves.

* * * * *

UNITED STATES PATENT AND TRADEMARK OFFICE
CERTIFICATE OF CORRECTION

| | | |
|---|---|---|
| PATENT NO. | : 12,364,497 B2 | Page 1 of 1 |
| APPLICATION NO. | : 17/937294 | |
| DATED | : July 22, 2025 | |
| INVENTOR(S) | : Michael R. Bailey et al. | |

It is certified that error appears in the above-identified patent and that said Letters Patent is hereby corrected as shown below:

In the Claims

| Column(s) | Line(s) | |
|---|---|---|
| 17 | 9 | Claim 3, delete "(f2)" and insert -- $(f_2)$ -- |
| 18 | 23 | Claim 15, delete "(f2)" and insert -- $(f_2)$ -- |

Signed and Sealed this
Fourth Day of November, 2025

John A. Squires
*Director of the United States Patent and Trademark Office*